United States Patent [19]

Brinker

[11] Patent Number: 5,433,718
[45] Date of Patent: Jul. 18, 1995

[54] ANTIBIOTIC ELUDING INTRAMEDULLARY NAIL APPARATUS

[76] Inventor: Mark Brinker, 233 Hamilton Station, Columbus, Ga. 31909

[21] Appl. No.: 934,114

[22] Filed: Aug. 20, 1992

[51] Int. Cl.⁶ .......................................... A61B 17/56
[52] U.S. Cl. ........................................ 606/62; 606/76
[58] Field of Search ................... 606/72, 73, 74, 75, 606/76, 77, 62–68

[56] References Cited

U.S. PATENT DOCUMENTS

| | | | |
|---|---|---|---|
| 4,281,420 | 8/1981 | Raab | 3/1.912 |
| 4,430,761 | 2/1984 | Niederer | 606/62 |
| 4,514,865 | 5/1985 | Harris | 606/62 |
| 4,535,487 | 8/1985 | Esper | 606/62 |
| 4,550,723 | 11/1985 | Belykh | 606/76 |
| 4,566,138 | 1/1986 | Lewis et al. | 623/22 |
| 4,713,076 | 12/1987 | Draenert | 606/67 |
| 4,851,008 | 7/1989 | Johnson | 606/62 |
| 4,863,444 | 9/1989 | Blomer | 606/76 |
| 4,919,666 | 4/1990 | Buchhorn | 606/76 |
| 4,976,258 | 12/1990 | Richter | 606/64 |
| 5,053,035 | 10/1991 | McLaren | 606/62 |
| 5,152,794 | 10/1992 | Davidson | 606/76 |

OTHER PUBLICATIONS

Steven F. Hoff, M.D. et al.–"The Depot Administration of Penicillin G and Gentamicin in Acrylic Bone Cement" dated Jun. 1981.
G. Josefsson, et al.–"Systemic Antibiotics and Gentamicin-Containing Bone Cement in the Prophylaxis of Postoperative Infections in Total Hip Arthroplasty" dated Sep. 1981.
Ralph Soto-Hall, M.D.–"Tobramycin in Bone Cement" dated May 1983.
Kevin L. Garvin, M.D. et al.–"Role of Gentamicin-Impregnated Cement in Total Joint Arthroplasty" dated Jul. 1988.
Jason H. Calhoun, M.D. et al.–"Antibiotic Beads in the Management of Surgical Infections" dated Apr. 1989.
Vilmos Vecsei, M.D. et al.–"Treatment of Chronic Osteomyelitis by Necrectomy and Gentamicin-PMMA Beads" dated Sep. 1981.
A. S. Baker, F.R.C.S., et al.–"Release of Gentamicin from Acrylic Bone Cement" dated Dec. 1988.
Eduardo A. Salvati, M.D. et al.–"Reimplantation in Infection" dated Jun. 1986.
William R. Murray, M.D.–"Use of Antibiotic-containing Bone Cement" dated Nov. 1984.

Primary Examiner—Michael A. Brown
Attorney, Agent, or Firm—Dick and Harris

[57] ABSTRACT

An antibiotic eluding intramedullary nail apparatus for use in the intramedullary fixation of fractured long bones, such as femurs, tibias, fibulas, humeri, ulnas and radii, as well as other orthopedic and bone reconstructive procedures, and, in particular fractures associated with an open wound exposing the soft tissue and medullary canal of the fractured bone to bacteria and other infectious micro-organisms. The apparatus includes an intramedullary nail to which is secured an antibiotic impregnated carrier compound, the apparatus being surgically insertable within the medullary canal of a fractured bone using conventional intramedullary nailing techniques thus providing a sustained localized release of antibiotic agents in bactericidial concentrations, and/or chemotherapeutic agents for bone tumors, directly within the medullary canal of the fractured bone and thereby serving to permit the use of intramedullary nailing to repair injuries which may be otherwise contraindicated due to the risk of deep wound and/or bone infections and/or bone tumors.

19 Claims, 1 Drawing Sheet

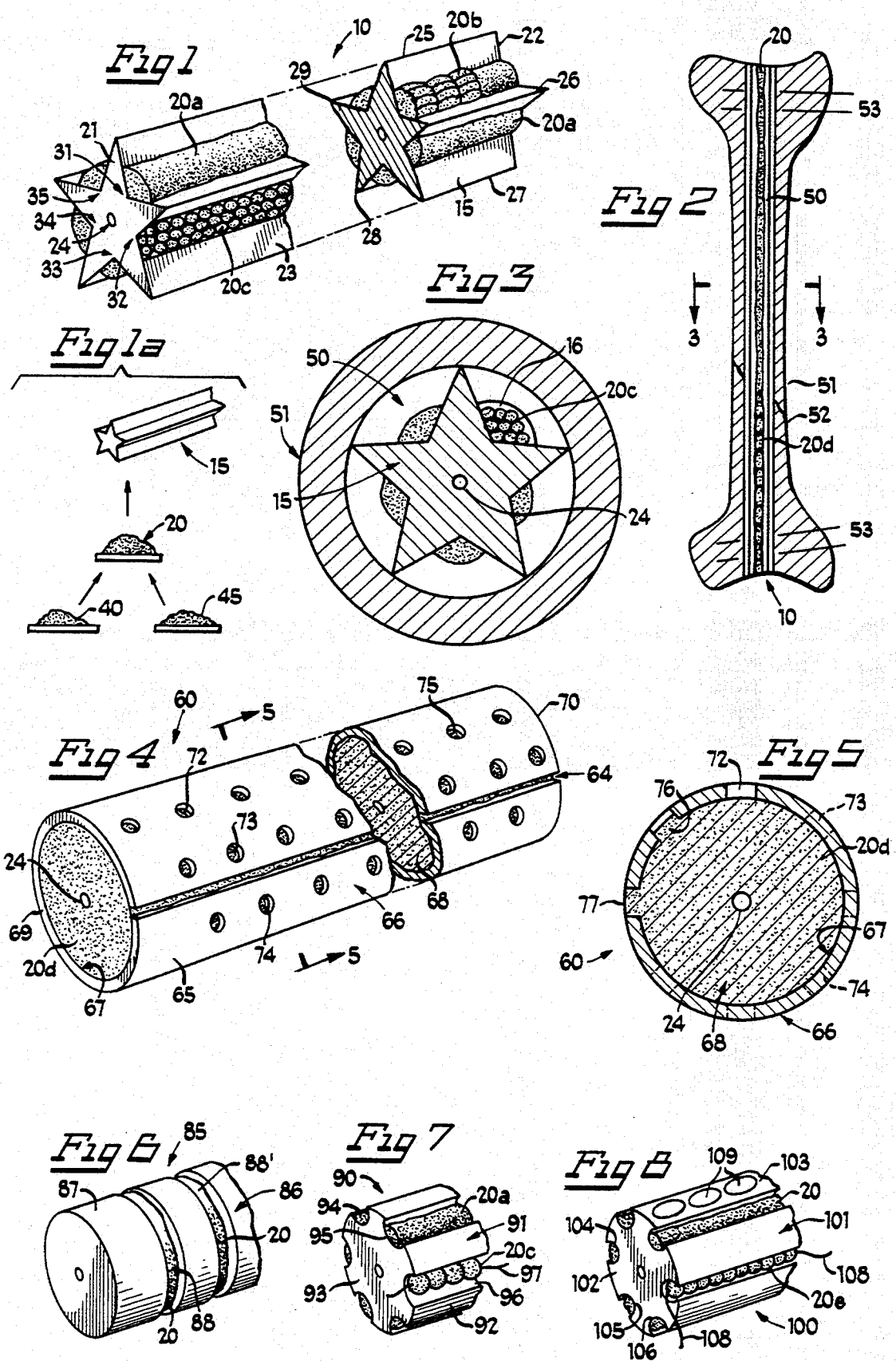

ANTIBIOTIC ELUDING INTRAMEDULLARY NAIL APPARATUS

BACKGROUND OF THE INVENTION

1. Field of the Invention

The present invention relates to bone fixation devices, and, more particularly, to an antibiotic eluding intramedullary nail apparatus and method of fabricating an antibiotic carrier compound and applying same to the intramedullary nail. The apparatus may be used for the intramedullary fixation of fractured long bones, such as femurs, tibias, fibulas, humeri, ulnas and radii, as well as in other orthopedic and bone reconstructive procedures, such as tumors, and, in particular fractures associated with an open wound exposing surrounding soft tissue and the medullary canal of the fractured bone to bacteria and other infectious micro-organisms.

2. Background Art

Fractures of the femur, tibia, fibula, as well as humeri, ulnas and radii are common injuries the treatment of which is typically dependent upon the cause of the injury, the exact nature of the fracture, the delay in receiving treatment and the presence of, or potential for, infection. In addition, fractures in immunocompromised and bone tumor patients often require special treatment to repair and/or prevent fractures. The present invention offers an opportunity to not only treat the fracture but further may be utilized to provide supplemental treatment by dispensing antibiotic or chemotherapeutic agents.

A favored method of treatment of fractures of long bones is intramedullary fixation. Intramedullary fixation involves the use of an intramedullary nailing system wherein an intramedullary nail or rod is surgically inserted within the medullary canal of the fractured bone and held in place through the use of pins or screws inserted through the opposing ends of the intramedullary nail. Once properly inserted, the intramedullary nail will function as a mechanical strut, or splint, which facilitates the natural union of the fractured bone by minimizing forces that would otherwise disrupt the union of the fractured bone.

An alternative method of treatment relies upon the use of external fixators. Typically, stabilizing rods are positioned external to the limb and in alignment with the fractured bone. The external stabilizing rods are held in position by fastening them to fixtures secured to the fractured limb above and below the location of the fracture. Unfortunately, external fixators have the potential disadvantage of being somewhat less stable than intramedullary rods due, in part, to external fixators being weight bearing versus being weight sharing, thus sometimes permitting the bone to shift resulting in an imperfect union or nonunion of the bone at the point or points of fracture. Internal fixation devices, such as intramedullary nails, typically offer increased stability of long bone fractures.

As is quite common, fractures of long bones often result in a portion of the fractured bone actually severing a portion of the skin resulting in an "open fracture". Unfortunately, even though such intramedullary nailing techniques have been quite successful in facilitating the natural union of fractured bones, obviating the need for external fixators or internal, but open wound forms of treatment such as plates and screws, the utilization of intramedullary nails is not always an option due to the risks of morbidity, and/or mortality which can occur from bacterial infestation in tissue and bone associated with open fractures. Indeed, when fractured bones either cause, are associated with or are exposed to open wounds, bacteria and/or other forms of infectious micro-organisms are given an "open door" not only into the wound, but also into the medullary canal of the fractured bone thereby increasing the risk of the bone itself becoming infected. Contraindications for intramedullary nailing of open long bone fractures include marked delays in treatment of the injury such that significant delays are deemed per se to give rise to infection rather than merely contamination, as well as contamination which cannot be thoroughly debrided.

Accordingly, in an attempt to combat actual infections or minimize the likelihood of infection in open wound situations, several procedures have been utilized in connection with intramedullary nailing. For example, when intramedullary fixation is to be relied upon, the wounded area, as well as the medullary canal of the bone itself, are typically cleansed by radical debridement and pulsed lavage irrigation prior to insertion of the intramedullary nail. Inasmuch as such cleansing does not necessarily completely combat the existence and/or formation of bacterial infestation in these areas, perioperative antibiotic therapy is usually administered systemically for three to five days following insertion of the nail and sometimes includes the application of antibiotic irrigation at the time of surgery—all in an attempt to "reduce" the surviving population of reproducing bacterial cells that escaped debridement. Unfortunately, antibiotics are not easily administered within the medullary canal of the fractured bone after it has been set with, or without, an intramedullary nail. Accordingly, any viable bacteria can result in severe complications to the patient. In addition, the inability to apply antibiotic therapy directly to the medullary canal with ease often necessitates the use of high systemic dose applications of antibiotics presenting the risk of allergy and other reactions resulting from high dose applications of antibiotics.

One technique which has been occasionally used to inhibit and/or destroy bacteria surrounding the open wound as well as any bacteria and bacterial cells which were not destroyed during debridement, is to attempt to directly repair the fractured bone with the use of a bone cement, such as bone cement formulated from polymethlmethacrylate (PMMA), wherein the bone cement has been mixed with an antibiotic, such as gentamicin, tobramycin, erythromycin, vancomicyn, oxacillin, cloxacillin, methicillin, lincomycin, ampicillin, or colistin. The "antibiotic bone cement" mixture is occasionally applied to the fractured bone and used to "artificially" cement the fractured bone together. As the cemented bone heals, the antibiotic will exude from the bone cement for a predetermined amount of time—thus enabling some exposure of the antibiotic within the medullary canal, albeit limited to the area immediately proximate to the point of fracture.

Although the use of an antibiotic bone cement mixture has been effective in fighting bacterial infestation, there are concerns with respect to the structural integrity of the bone cement itself when the antibiotics are mixed therewith. Indeed, the utilization of too much of an antibiotic could quite conceivably result in a reduction in the tensile and compressive strength of the bone cement. Accordingly, such a condition could facilitate fatigue at the cemented region of the "repaired" bone.

Additionally, the use of bone cement may potentially result in the formation of scar tissue proximate to the cemented region.

In addition to utilizing such "antibiotic bone cement" mixtures for facilitating structural cemented unity of fractured bones, such mixtures have more commonly been utilized in "non-structural" applications as well. Antibiotic cement mixtures have been formed immediately prior to surgery into beads strung together on surgical grade wire. The string of "antibiotic beads" may thus be inserted into an open wound (which may have been caused by a bone fracture, or even from an incision during surgery), wherein the desired antibiotic is capable of release from the hardened cement after such insertion. Again, such an application is limited to application of antibiotic therapy external to the medullary canal. Moreover, antibiotic beads most always must be removed from the patient due to the risk that the beads may become dislodged and migrate from the point of insertion. More importantly, there is evidence that beads remaining in soft tissue will, over time, become surrounded by dense fibrous tissue both reducing the therapeutic effect of the antibiotic as well as causing discomfort to the patient. An example of such an antibiotic cement compound bead is Gentamicinpolymethylmethacrylate ("G-PMMA"). Although such "beads" have been effective against bacteria surrounding the open wound, they are not intended for use within the medullary canal of the bone, let alone are they intended for cooperation with an intramedullary nail or other type of structural bone support device.

A further prior art use of mixtures of antibiotics and bone cement is in connection with total joint arthoplasty, e.g. hip replacement. In this prior art application, the bone cement is used primarily for its cement—structural property where the inclusion of an antibiotic serves to mitigate or fight a present infection minimizing the opportunity for infection to cause a mechanical failure of the implant.

Such uses of antibiotic cement in joint arthoplasty is apparently limited to providing antibiotic administration locally at the point of contact between the prosthesis and surrounding bone and tissue and is not intended to provide antibiotic application to areas deep within the medullary canal.

SUMMARY OF THE INVENTION

The present invention comprises an antibiotic eluding intramedullary nail apparatus for use in association with the intramedullary fixation of fractured long bones, such as fractured femurs, tibias, fibulas, humeri, ulnas and radii, having a medullary cavity, wherein the fracture may be associated with an open wound, which in turn, may expose the medullary cavity within the fractured bone, as well as the soft tissue surrounding the open wound, to bacteria and/or other infectious microorganisms which could result in morbidity as well as mortality. The present invention has further application in treating failed total hip and knee arthoplasty, infected non-unions and malunions, osteomyelitis, fractures in immunocompromised patients, as well as treating pathologic fractures with chemotherapeutic agents caused by tumors which have weakened the bone.

The antibiotic eluding intramedullary nail apparatus comprises means for stabilizing the fractured bone in an aligned position. In the first embodiment of the invention, the bone stabilizing means comprises an intramedullary nail having a first end, a second end and an exterior surface, wherein only a portion of the exterior surface of the intramedullary nail is in juxtaposition with at least a portion of the interior surface of medullary cavity of the fractured bone. The distal end of the intramedullary nail may further be tapered and/or flexible to facilitate insertion into the medullary canal of the fractured long bone.

The antibiotic eluding intramedullary nail apparatus further includes bactericidial means for inhibiting the growth of and/or destroying bacteria, the continued presence of which may result in an infection in the medullary cavity of the fractured bone as well as the soft tissue proximate the fracture. The bactericidal means is combined with a carrier means to form an antibiotic compound which is, in turn, secured to the intramedullary nail.

The carrying means preferably consists of a material which is not only biocompatible, but which will also facilitate exudation of the bactericidal means towards inhibiting the growth of and destroying bacteria.

It is contemplated that the antibiotic carrier compound may be secured to the intramedullary nail either immediately before its use in a surgical procedure or well in advance such that the completed assembly may be handled in a "ready-to-use" fashion. Alternatively, it is contemplated that chemotherapeutic agents could be combined with, and/or replace, a bactericidal compound in cases of a bone tumor.

In use, the bone stabilizing means together with the antibiotic carrier compound is inserted within the medullary cavity of the fractured bone where the bactericidal means for inhibiting the growth of and destroying bacteria will continuously exude from the carrier means for at least a predetermined period of time following insertion and closure of the wound.

In one embodiment of the invention, the bone stabilizing means has a star-like transverse cross-sectional configuration. This star-like shape includes a plurality of points and corresponding "v-shaped" depressions between adjacently positioned ones of the points. Accordingly, the antibiotic carrier compound is positioned below at least two adjacently positioned ones of the points so as to preclude direct contact of the carrier means with the interior surface of the medullary cavity of the fractured bone after the bone stabilizing means has been positioned within the medullary cavity.

In another embodiment of the invention, the bone stabilizing means has one or more grooves which are integrally formed within the exterior surface. These grooves may be positioned in substantially parallel alignment with the longitudinal axis of the bone stabilizing means or they may be positioned in concentric alignment with the longitudinal axis. Of course, other orientations of the grooves are also contemplated. The antibiotic carrier compound is operably positioned within at least a portion of the one or more grooves so as to preclude direct contact of the carrier means with the medullary cavity of the fractured bone after the bone stabilizing means has been operably positioned within the medullary cavity. These grooves may be of virtually any shape, though they are contemplated as being either "U" shaped or "C" shaped, wherein "C" shaped groves may serve to retain the antibiotic compound in place.

In one embodiment of the invention, the bone stabilizing means comprises a hollow shaft having an internal region defined by an interior surface. The hollow shaft has one or more apertures depending from the internal region and extending through the interior surface and the exterior surface. The antibiotic carrier compound is positioned within the internal area so as to preclude direct contact of the carrier means with the medullary cavity of the fractured bone. Accordingly, the apertures enable directed exudation of the means for inhibiting and destroying bacteria from the carrier means to the medullary cavity.

The bone stabilizing means may include an opening depending from the internal region and extending through the interior surface and the exterior surface and extending longitudinally from the first end to the second end of the bone stabilizing means to permit the bone stabilizing means to flex thereby facilitating its insertion into the medullary canal. The antibiotic compound means may be formed of a segmented rod to permit flexing to preclude splitting or breaking of the antibiotic compound means during insertion into the medullary canal. The antibiotic compound means positioned within the internal area of the hollow shaft may be cannulated to permit passage of a guide wire toward facilitating insertion of the apparatus into the medullary canal.

The bactericidal means is contemplated as being selected from the group of antibiotics consisting of gentamicin, tobramycin, erythromycin, vancomicyn, oxacillin, cloxacillin, methicillin, lincomycin, ampicillin, and colistin although others may be used.

In one embodiment of the invention the carrier means further includes an ingredient such as barium sulfate which serves to render the carrier means radio opaque.

In yet another embodiment of the invention the antibiotic compound means which is secured to at least a portion of the bone stabilizing means is formed so as to have an irregular external surface thereby increasing the surface area of said antibiotic compound means to, in turn, increase the degree to which said bactericidal means is released from the antibiotic compound means. The antibiotic compound means may for example be formed into a plurality of spherical shaped elements thereby increasing the surface area of said antibiotic compound means to, in turn, increase the degree to which said bactericidal means is released from said antibiotic compound means.

The present antibiotic eluding intramedullary nail apparatus may further include a retaining means affixed to the bone stabilizing means proximate to the antibiotic compound means to retain any portion of said antibiotic compound means which becomes dislodged from the bone stabilizing means either during insertion of the apparatus into the medullary canal or subsequent to implantation.

In addition to affixing the antibiotic compound to the external surface of the bone stabilizing means, it is within the scope of the present invention to include depressions formed into the external surface of the bone stabilizing means into which may be positioned the antibiotic compound means. In addition, the bone stabilizing means may be cannulated to permit passage of a guide wire toward facilitating insertion of the apparatus into the medullary canal. To permit flexing of the bone stabilizing means as may be desirable to facilitate insertion into the medullary canal the bone stabilizing means may be formed of a malleable material.

In the preferred embodiment of the invention, the carrier means comprises bone cement. Such bone cement is commercially available and may be formulated from polymethlmethacrylate (PMMA). Additionally, the bactericidal means for inhibiting the growth of and destroying bacteria may be combined with the bone cement by uniform saturation and/or impregnation. Furthermore, it is contemplated that the bone cement be selected from the group consisting of cement compounds which facilitate exudation of antibiotics or, other medications, prior to substantial curing of the cement.

The present invention further comprises a method of fabricating an antibiotic eluding intramedullary nail apparatus for use in the intramedullary fixation of fractured long bones, such as femurs, tibias and fibulas, and, in particular fractures associated with an open wound exposing the soft tissue and medullary canal of the fractured bone to bacteria and other infectious micro-organisms. The method comprises the steps of first utilizing a bone stabilizing element having an exterior surface and one or more depressed regions extending below the exterior surface of the bone stabilizing element, combining an antibiotic agent with a carrier agent so as to form an antibiotic compound, the carrier agent being of the type which allows for release of the antibiotic agent after the antibiotic compound has substantially cured. The antibiotic compound is then applied to at least a portion of the one or more depressed regions extending below the exterior surface of the shaft and the antibiotic compound is allowed to substantially cure.

In the preferred embodiment of the invention, the shaft has a plurality of points and corresponding "v-shaped" depressions extending below and between adjacently positioned ones of the points. The antibiotic carrier compound is then applied adjacent one or more of the plurality of "v-shaped" depressions, and, in turn, below corresponding ones of the points.

In another preferred embodiment invention, the shaft has an interior surface which defines an internal region, and, one or more apertures depending from the internal region. The apertures extend through an adjacent portion of the interior and exterior surfaces. The antibiotic carrier compound is then applied within the internal region adjacent at least one of the one or more apertures.

The present invention is further contemplated for use with immunocompromised and bone tumor patients wherein chemotherapeutic agents may be mixed with the bone cement, secured to the bone stabilizing means and inserted into the medullary canal. By this technique such chemotherapeutic agents may be eluded within the canal toward providing additional treatment toward treating pathologic fractures or preventing such a fracture. In connection with failed total hip and/or knee arthoplasty which are triggered by an established infection, the present invention may be used to provide treatment between the time the failed prosthesis is removed and a replacement provided. Particularly, a form of the invention may be inserted into the medullary canal after the hip or knee prosthesis has been removed so as to provide for the application of antibiotic agents directly within the medullary canal thereby providing superior performance over beads which are difficult to place deep within the canal and difficult to remove. When prudent, the invention may be removed from the canal and the replacement prosthesis re-inserted.

BRIEF DESCRIPTION OF THE DRAWINGS

For a better understanding of the present invention, reference may be had to the accompanying drawings in which:

FIG. 1 is a perspective view of an embodiment of the present antibiotic eluding intramedullary nail apparatus;

FIG. 1a is a schematic developmental view of the present invention, showing in particular, the formation of the antibiotic compound and its positioning on the intramedullary nail;

FIG. 2 is an elevated cross-sectional view of the embodiment shown in FIG. 1, as operably inserted within the medullary canal of a fractured long bone;

FIG. 3 is a cross-sectional view taken generally along lines 3—3 of FIG. 2;

FIG. 4 is a perspective view of an embodiment of the present invention;

FIG. 5 is a cross-sectional view taken generally along lines 5—5 of FIG. 4;

FIG. 6 is a fragmentary view of an embodiment of the present invention;

FIG. 7 is a fragmentary view of an embodiment of the present invention; and

FIG. 8 is a fragmentary view of an embodiment of the present invention.

DETAILED DESCRIPTION OF THE DRAWINGS

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments illustrated.

Antibiotic eluding intramedullary nail apparatus 10 is shown in FIG. 1 as comprising bone stabilizing means 15 to which is secured antibiotic compound 20 in forms 20a, 20b and 20c. Bone stabilizing means 15 is shown including first end 21, second end 22 and exterior surface 23. Bone stabilizing means 15 is further shown to be cannulated, i.e. possessing a hollow passage 24 extending from the first end 21 to the second end 22 capable of accepting passage of a guide wire as sometimes used to facilitate insertion of bone stabilizing means 15 into the medullary canal 50 (FIG. 3). In one embodiment of the invention, bone stabilizing means 15 comprises and is illustrated having a star-shaped cross-sectional configuration comprising a plurality of points 25 through 29, and a plurality of "v-shaped" depressions 31 through 35—each of which regions are positioned between and extend below two adjacent ones of the points. For purposes of illustration, bone stabilizing means 15 is shown in a magnified configuration having a five pointed star configuration while in practice it may, for example, include twenty or more points each with a smaller peak-to-valley dimension. Furthermore, although bone stabilizing means 15 is shown as having a star-shaped configuration other shapes, such as cylindrical, clover, and other substantially symmetrical, as well as non-symmetrical configurations are also contemplated. Furthermore, it is also contemplated that bone stabilizing means 15 may be constructed from any commercially acceptable biocompatible alloy and/or composite material which is substantially torsionally rigid and which possesses relatively heavy load-bearing capabilities. Alternatively, the bone stabilizing means 15 may be constructed from a malleable material to permit some limited flexing to facilitate its insertion into the medullary canal 50.

Antibiotic compound 20 is shown in FIG. 1a being formed of the combination of bactericidal means 45, an antibiotic selected from the group including but not limited to gentamicin, tobramycin, erythromycin, vancomycin, oxacillin, cloxacillin, methicillin, lincomycin, ampicillin, or colistin, for inhibiting the growth of and-/or destroying bacteria, and carrier means 40 for sustainably releasing bactericidal means 45 into the medullary canal. Alternatively, bactericidal means 45 may further include or be replaced with a chemotherapeutic agent for treating cancerous cells and bone tumors.

Since the degree to which antibiotic compound 20 eludes bactericidal means 45 is a function of the surface area exposed within the medullary canal, it is contemplated that the antibiotic compound may be formed with varying surface configurations to maximize or otherwise control the release of bactericidal means 45. Antibiotic compound 20a is shown having a smooth surface 20a while antibiotic compound 20b is shown having an irregular "mounded" surface 20b. Other surface configurations, such as corrugated or rippled are deemed within the scope of the present invention. It is further contemplated that antibiotic compound 20 may be formed of beads 20c thereby maximizing the surface area of the compound exposed within the medullary canal 50. The beads 20c may be individually formed and thereafter disposed upon bone stabilizing means 15 prior to fully curing toward their retaining their position upon the bone stabilizing means 15. A retaining means 16 (FIG. 3) is shown positioned over antibiotic compound 20c and affixed to bone stabilizing means 15 by inserting the ends into a groove formed into bone stabilizing means 15 toward serving to retain any beads which may become dislodged from their predisposed position. Retaining means 16 may comprise any suitable biocompatible material. The antibiotic compound 20 may be affixed to bone stabilizing means 15 by action of bone cement. The surface of bone stabilizing means 15 which is to accept antibiotic compound 20 may alternatively be "roughened" to provide a better adherence. Alternatively, an adhesive may be used to affix the antibiotic compound 20 to bone stabilizing means 15 if necessary.

In the preferred embodiment of the invention bactericidal means 45 comprises an antibiotic and it is contemplated that any suitable antibiotic may be used including but not limited to gentamicin, tobramycin, erythromycin, vancomycin, oxacillin, cloxacillin, methicillin, lincomycin, ampicillin, colistin, among others. Of course the choice of antibiotic may depend upon the source of an actual infection or potential infection. Likewise, carrier means 40 preferably consists any conventional biocompatible bone cement, such as polymethylmethacrylate (PMMA), which will reliably mix with antibiotics. Inasmuch as PMMA undergoes a polymerization process and an exothermic reaction only antibiotics which are thermostable should be used. Antibiotics which might be deactivated by the polymerization process should be avoided. In addition, other types of biocompatible carrier means, other than bone cement, which will release/exude antibiotics and/or other forms of medication within the medullary canal of the bone are also contemplated and are deemed within the scope of the present invention.

Carrier means 40 and bactericidal means 45 are mixed with each other in order to form antibiotic compound 20. In the preferred embodiment of the invention antibiotic compound 20 is prepared, secured to bone stabilizing means 15 and allowed to fully cure well in advance of its use in a surgical procedure such that apparatus 10 may be handled as a "ready-to-use" product. Varying concentrations of bactericidal means 45 may be used such that apparatus 10 may be made available in different formulations. It is additionally contemplated that antibiotic compound 20 may be prepared by the surgeon on a "custom basis" just prior to its use whereby the concentration of bactericidal means may be tailored to the individual patents needs. Bactericidal means may be combined with or replaced by a chemotherapeutic agent to provide treatment of bone tumors or other cancerous conditions.

FIG. 2 and FIG. 3 of the drawings illustrate the present antibiotic eluding intramedullary nail apparatus 10 positioned within medullary canal 50 of fractured bone 51. As can be seen in FIG. 2, antibiotic compound 20 is positioned on bone stabilizing means 15 at a portion below corresponding ones of points 25 through 29, intentionally out of direct contact with the interior surface of medullary canal 50. Indeed, it is preferable that antibiotic compound 20 does not protrude above the outer most surface of the bone stabilizing means 15 so as to preclude sheering forces from bearing upon antibiotic compound 20 which may otherwise dislodge the compound from the bone stabilizing means 15. In addition, in the event that the bone cement has not fully cured prior to insertion into the canal, such a construction may further preclude the antibiotic compound 20 from cementing bone stabilizing means 15 in position within the medullary canal 50. In addition, it is contemplated that such spaced apart positioning will facilitate exudation of the antibiotic from the bone cement 45 and migration of the antibiotic 40 within the localized area proximate to the fracture 52. Pins/screws 53 are shown fixing bone stabilizing means 15 in place within medullary canal 50. Any adhering of stabilizing means 15 to medullary canal 50 could result in the inability to remove antibiotic eluding intramedullary nail apparatus 10, as is often desirable after the bones of younger patients have healed. While illustrated as being substantially straight, bone stabilizing means 15 may be curved or otherwise formed to match the shape of the bone and/or the medullary canal.

Four alternative embodiments of the antibiotic eluding intramedullary nail apparatus are shown in FIG. 4 through FIG. 8. Specifically, antibiotic eluding intramedullary nail apparatus 60 is shown in FIG. 4 and FIG. 5 as comprising bone stabilizing means 65 having an open internal region 68 into which antibiotic compound means 20 is disposed. Bone stabilizing means 65, includes exterior surface 66, interior surface 67, internal region 68 which is defined by interior surface 67, first end 69, second end 70 and a plurality of apertures, such as apertures 72 through 77. In order to permit bone stabilizing means 65 to flex when being inserted into the medullary canal, bone stabilizing means 65 optionally includes a gap 64 extending longitudinally from the first end 69 to the second end 70. As shown more clearly in FIG. 5, each of the apertures, such as apertures 72 and 73, depend from internal region 68 and extend through and past interior surface 67 and exterior surface 66. Antibiotic compound 20d, formulated in the manner previously described, is shown positioned within internal region 68 of bone stabilizing means 65 and is further shown to be optionally cannulated, i.e. possessing a hollow passage 24 extending from the first end 69 to the second end 70 and capable of accepting passage of a guide wire as sometimes used to facilitate insertion of bone stabilizing means 15 into the medullary canal.

Accordingly, after antibiotic eluding intramedullary nail apparatus 60 is inserted within the medullary canal of a fractured bone, bactericidal means 45 will exude from carrier means 40 through apertures, such as apertures 72 through 77, as well as past first and second ends 69 and 70, respectively of bone stabilizing means 65. It is preferred that antibiotic compound 20 be positioned at least even with or below exterior surface 66 of bone stabilizing means 65 so as to avoid direct physical abutment of antibiotic compound 20 with the walls of the medullary canal and preclude any protruding antibiotic compound 20 from being sheered off during insertion into the medullary canal as illustrated in apertures 77 and 76, respectively. It is contemplated that antibiotic compound may be prepositioned with bone stabilizing means 65 prior to insertion into medullary canal 50, or alternatively, that antibiotic compound may be injected into internal region 68 after bone stabilizing means 65 is positioned in place. Should a flexible bone stabilizing means 65 be utilized, it is contemplated that antibiotic compound 20d positioned within internal region 68 may be formed as a segmented rod 20d, (FIG. 2), capable of flexing without unduly discharging fragments of antibiotic compound 20.

Antibiotic eluding intramedullary nail apparatus 85 is shown in FIG. 6 as comprising bone stabilizing means 86 having exterior surface 87 and a plurality of grooves, such as grooves 88 and 88'. Bone stabilizing means 86 may optionally be cannulated to permit passage of a guide wire. Each of the grooves are concentrically positioned with respect to the longitudinal axis of the bone stabilizing means 86 and depend below exterior surface 87—so as to enable operable positioning of antibiotic compound 20 therein without the antibiotic carrier compound inadvertently extending above exterior surface 87. Although not shown, a plurality of grooves may be concentrically positioned along the entire length of bone stabilizing means 86. Alternatively, variances in the number of grooves, as well as the width, depth, and positioning along the surface of bone stabilizing means 86 are also contemplated.

Antibiotic eluding intramedullary nail apparatus 90 is shown in FIG. 7 as comprising bone stabilizing means 91 and antibiotic compound 20. Bone stabilizing means 91 includes first end 93, exterior surface 92 and a plurality of substantially U-shaped grooves, such as grooves 94 through 96. Bone stabilizing means 91 may optionally be cannulated to permit passage of a guide wire. While each of these grooves may extend the entire length of the bone stabilizing means, grooves being shorter in length as well as varying in depth, are also contemplated. In an alternative embodiment of the invention, antibiotic compound 20 is formed into beads 20e and strung on surgical grade wire or suture 97 wherein the strand of beads may be positioned within one or more grooves as illustrated by groove 96.

Antibiotic eluding intramedullary nail apparatus 100 is shown in FIG. 8 as including bone stabilizing means 101 and antibiotic compound 20. Bone stabilizing means 101 includes first end 102, exterior surface 103 and a plurality of substantially C-shaped retaining grooves, such as grooves 104 through 107. Bone stabilizing means 101 may optionally be cannulated to permit passage of a guide wire. Such grooves may extend the entire length of bone stabilizing means 101, or alternatively, they may be shorter or vary in length provided they are open to at least one end of bone stabilizing means 101. It is contemplated that antibiotic compound 20 be fabricated having a rod-shaped construction and having a cross-section corresponding to the shape of grooves 104 to thereby facilitate their insertion into the C-shaped grooves 104–107. C-shaped grooves 104 through 107 will restrict the rod-shaped antibiotic carrier compound from inadvertent release—unless they are pushed through the ends, such as first end 102, of bone stabilizing means 101. In an alternative embodiment of the invention, antibiotic compound 20 is formed into beads 20e and strung on surgical grade wire or suture 108 wherein the strand of beads may be positioned within one or more C-shaped grooves as illustrated and wherein the diameter of the beads is preferably larger than the longitudinal opening of the groove thereby serving to preclude the beads from being dislodged. In another embodiment of the invention, apertures 109 may be formed into the external surface of the bone stabilizing means 101 into which antibiotic compound 20 may be disposed toward administering further quantities and/or types of bactericidal or other agents such as chemotherapeutic compounds.

Fabrication of antibiotic eluding intramedullary nail apparatus 10 and particularly antibiotic compound 20 may be performed in a commercial setting and stored and transported to surgical units in a "ready-to-use" package. Alternatively, antibiotic compound 20 may be prepared by appropriate surgical or pharmaceutical staff to suit the needs of a particular patient. Antibiotics and bone cement are typically mixed in powered form before the liquid component of the bone cement is added to thus insure an even mixture of antibiotic within the cement. Studies have revealed that excessive amounts of powdered antibiotic in proportion to the bone cement may reduce the strength of the bone cement or otherwise effect its handling characteristics. Since the present invention uses bone cement only for its proven ability to deliver antibiotics in a sustained release manner and does not utilize bone cement for its bonding strength variable proportions of antibiotic and cement may be freely used. Although bone cement may be used, any other type of biocompatible carrier is also contemplated for use—provided that it facilitates the sustained release of the antibiotic it is combined with. Examples of various types of antibiotics for use in the formation of antibiotic compound 20 include, but are not limited to, gentamicin, tobramycin, erythromycin, vancomicyn, oxacillin, cloxacillin, methicillin, lincomycin, ampicillin, and colistin. In addition, other types of medication such as chemotherapeutic agents (other than antibiotics) which may be desirable for release from the bone cement, or other type of carrier means, are also contemplated for use.

After antibiotic compound 20 is formed, it is applied to at least a portion of the region below the exterior surface of the bone stabilizing means 15, such as the: "v-shaped" depressions 31 through 35 of bone stabilizing means 15 (FIG. 1); internal region 68 of bone stabilizing means 65 (FIG. 5); and/or the grooves, such as grooves 88, 94 and 104 of bone stabilizing means 86, 91 and 101, respectively, of FIGS. 6 through 8, respectively. Once antibiotic compound 20 is positioned with the bone stabilizing means, it is then allowed to substantially cure (although, it is also contemplated that such curing occur prior to such positioning). After such curing has occurred, the antibiotic eluding intramedullary nail apparatus can then be inserted within the medullary canal of the fractured bone where the antibiotics will exude from the bone cement for a continuous, predetermined period of time, to, in turn, inhibit the growth of and/or destroy bacteria within the medullary canal as well as around the wound.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An antibiotic eluding intramedullary nail apparatus for use in association with the intramedullary fixation of fractured long bones, such as fractured femurs, tibias, fibulas, humeri, ulnas and radii having a medullary canal, wherein the fracture may be associated with an open wound, which in turn, may expose the medullary canal within the fractured bone, as well as the area surrounding the open wound, to bacteria and/or other infectious micro-organisms which could result in morbidity as well as mortality, said antibiotic eluding intramedullary nail apparatus comprising:

means for stabilizing the fractured bone in an aligned position, said bone stabilizing means having a first end, a second end and an exterior surface, wherein said bone stabilizing means is positionable within the medullary canal of the fractured bone;

said bone stabilizing means having a plurality of "C" shaped grooves integrally formed in the exterior surface of said bone stabilizing means extending longitudinally from said first and to said second end of said bone stabilizing means;

antibiotic compound means, said antibiotic compound means including bactericidal means for inhibiting the growth of and destroying bacteria which may result in an infection in the medullary canal of the fractured bone as well as proximate the open wound associated with the fracture, and carrier means for sustainably releasing said bactericidal means;

said antibiotic compound means dimensioned so as to be effectively retained within said plurality of c-shaped grooves to in turn be capable of being operably and releaseably positionable within at least a portion of the plurality of c-shaped grooves to facilitate removal and/or replacement of said antibiotic compound, so as to permit said bactericidal means to be eluded directly into the medullary canal upon insertion and alignment of said apparatus within said canal.

2. The invention according to claim 1 wherein said antibiotic compound is formed into a plurality of generally spherical shaped beads strung together using surgical grade wire.

3. The invention according to claim 1 wherein said antibiotic compound is formed into a plurality of generally spherical shaped beads strung together using surgical grade suture.

4. The invention according to claim 1 in which said carrier means comprises bone cement.

5. The invention according to claim 4 in which said bactericidal means is combined with the bone cement by uniformly saturating said bactericidal means within the bone cement.

6. The invention according to claim 4 in which the bone cement is selected from the group consisting of cement compounds which facilitate exudation of antibiotics wherein said antibiotics can be combined with the bone cement prior to substantial curing of the bone cement.

7. The invention according to claim 1 in which said bactericidal means is selected from the group of antibiotics consisting of gentamicin, tobramycin, erythromycin, vancomicyn, oxacillin, cloxacillin, methicillin, lincomycin, ampicillin, and colistin.

8. The invention according to claim 1 in which said carrier means further includes an ingredient to render same radio opaque.

9. The invention according to claim 8 wherein said ingredient is barium sulfate.

10. The invention according to claim 1 in which said bone stabilizing means comprises an intramedullary nail.

11. The invention according to claim 1 in which said bone stabilizing means is cannulated to permit passage of a guide wire toward facilitating insertion of the apparatus into the medullary canal.

12. The invention according to claim 1 in which said bone stabilizing means is malleable to permit flexing toward facilitating insertion of the apparatus into the medullary canal.

13. The invention according to claim 1 wherein said antibiotic compound means further includes a chemotherapeutic agent.

14. An antibiotic eluding intramedullary nail apparatus for use in association with the intramedullary fixation of fractured long bones, such as fractured femurs, tibias, fibulas, humeri, ulnas and radii having a medullary canal, wherein the fracture may be associated with an open wound, which in turn, may expose the medullary canal within the fractured bone, as well as the area surrounding the open wound, to bacteria and/or other infectious micro-organisms which could result in morbidity as well as mortality said antibiotic eluding intramedullary nail apparatus comprising:

means for Stabilizing the fractured bone in an aligned position, said bone stabilizing means comprising a hollow shaft having an internal region defined by an interior surface, a first end, a second end and an exterior surface, wherein said bone stabilizing means is positionable within the medullary canal of the fractured bone;

said hollow shaft having a plurality of apertures depending from said internal region and extending through said interior surface and said exterior surface;

antibiotic compound means, said antibiotic compound means including bactericidal means for inhibiting the growth of and destroying bacteria which may result in an infection in the medullary canal of the fractured bone as well as proximate the open wound associated with the fracture, and carrier means for sustainably releasing said bactericidal means;

and wherein said antibiotic compound is operably positioned within the internal area of the hollow shaft so as to preclude direct contact of said antibiotic compound means with the medullary canal of the fractured bone and to preclude said antibiotic compound means from becoming dislodged during insertion of said apparatus into the medullary canal, and, to in turn, enable the release of the bactericidal means through at least one of said apertures.

15. The invention according to claim 14 wherein said bone stabilizing means further includes an opening depending from said internal region and extending through said interior surface and said exterior surface and extending longitudinally from said first end to said second end of said bone stabilizing means to permit said bone stabilizing means to flex thereby facilitating its insertion into said medullary canal.

16. The invention according to claim 14 wherein said antibiotic compound means is formed of a segmented rod to permit flexing to preclude splitting or breaking of said antibiotic compound means during insertion into said medullary canal.

17. The invention according to claim 14 in which said antibiotic compound means operably positioned within the internal area of the hollow shaft is cannulated to permit passage of a guide wire toward facilitating insertion of the apparatus into the medullary canal.

18. A method of fabricating an antibiotic eluding intramedullary nail apparatus for use in the intramedullary fixation of fractured long bones, such as femurs, tibias and fibulas, humeri, ulnas and radii, and, in particular fractures associated with an open wound exposing the soft tissue and medullary canal of the fractured bone to bacteria and other infectious micro-organisms wherein an antibiotic agent is sustainably released directly into the medullary canal of fractured bones toward preventing and combating bacterial infestation of the bone and/or surrounding area, which could result in morbidity and mortality, said method comprising the steps of:

utilizing a bone stabilizing element having an exterior surface having a plurality of points and corresponding "v-shaped" depressions extending below and between adjacently positioned ones of the points;

combining an antibiotic agent with a carrier agent so as to form an antibiotic compound, said carrier agent being of the type which allows for release of said antibiotic agent after said antibiotic compound has substantially cured;

applying the antibiotic compound into at least one of said one or more plurality of "v-shaped" depressions, and, in turn, below corresponding ones of the points; and allowing the antibiotic compound to substantially cure.

19. A method of fabricating an antibiotic eluding intramedullary nail apparatus for use in the intramedullary fixation of fractured long bones, such as femurs, tibias and fibulas, humeri, ulnas and radii, and, in particular fractures associated with an open wound exposing the soft tissue and medullary canal of the fractured bone to bacteria and other infectious micro-organisms wherein an antibiotic agent is sustainably released directly into the medullary canal of fractured bones toward preventing and combating bacterial infestation of the bone and/or surrounding area, which could result in morbidity and mortality, said method comprising the steps of:

utilizing a bone stabilizing element having an interior surface defining an internal region extending from a first end to a second end of said bone stabilizing element, and, a plurality of apertures depending from the internal region and extending through an adjacent portion of the interior and exterior surfaces;

combining an antibiotic agent with a carrier agent so as to form an antibiotic compound, said carrier agent being of the type which allows for release of said antibiotic agent after said antibiotic compound has substantially cured;

applying said antibiotic compound within the internal region adjacent at least one of the plurality of apertures; and allowing the antibiotic compound to substantially cure.

* * * * *